United States Patent [19]

Baldoni et al.

[11] Patent Number: 5,084,446
[45] Date of Patent: Jan. 28, 1992

[54] ALUMINUM COMPLEX OF POLYSULFONATED SUCROSE

[75] Inventors: John M. Baldoni, Wrightsville Beach; Nick V. Lazaridis, Wilmington, both of N.C.

[73] Assignee: Applied Analytical Industries, Inc., Wilmington, N.C.

[21] Appl. No.: 381,795

[22] Filed: Jul. 19, 1989

Related U.S. Application Data

[63] Continuation-in-part of Ser. No. 236,167, Aug. 25, 1988, abandoned, and a continuation-in-part of Ser. No. 285,028, Dec. 16, 1988, Pat. No. 4,990,610.

[51] Int. Cl.$^5$ .................. C07H 11/00; C07H 13/12; A61K 31/715
[52] U.S. Cl. ........................ 514/53; 536/118
[58] Field of Search .............. 536/118; 514/54, 53

[56] References Cited

U.S. PATENT DOCUMENTS

| | | | |
|---|---|---|---|
| 3,271,388 | 9/1966 | Cammarata et al. | 536/118 |
| 3,432,489 | 3/1969 | Nitta | 536/118 |
| 3,720,659 | 3/1973 | Guiseley et al. | 536/118 |
| 4,885,361 | 12/1989 | Wessel | 536/118 |
| 4,940,786 | 7/1990 | Duff | 536/117 |
| 4,948,881 | 8/1990 | Naggi et al. | 536/118 |

OTHER PUBLICATIONS

Morikawa et al. (1981), J. Chem. Soc. (Faraday), vol. 77, pp. 629-639.
Nagashima, R. (1981), J. Clin. Gastroenteral., vol. 3, pp. 103-110.
Nagashima et al, (1979), Arzheim, Forsch., vol. 29, pp. 1668-1675.

Primary Examiner—Johnnie R. Brown
Assistant Examiner—Gary L. Kunz
Attorney, Agent, or Firm—William H. Edgerton

[57] ABSTRACT

A sucralfate-like chemical compound which is free flowing but turns viscid upon contact with acid or non-acid aqueous liquid. The compound is prepared by adding an excess of aluminum chlorohydrate to sucrose octaammonium sulfate in aqueous alcohols.

7 Claims, 4 Drawing Sheets

ALUMINUM COMPLEX OF POLYSULFONATED SUCROSE

This application is a continuation-in-part of Ser. No. 07/236,167, filed Aug. 25, 1988, now abandoned and of Ser. No. 07/285,028 filed Dec. 16, 1988, now U.S. Pat. No. 4,990,610.

A new chemical entity has been invented which is related to the broad class of molecules known as polysulfonated carbohydrate aluminum complexes. The most well-known of this class of molecule is sucralfate, a pharmaceutical product marketed for the treatment of duodenal ulcers. This new molecule is closely related in structure to sucralfate but has distinct physicochemical properties. This invention describes the new chemical entity and the process by which it can be reproducibly prepared.

BACKGROUND OF THE INVENTION

Sulfonated carbohydrates have been widely reported in the literature. The literature on aluminum complexes of polysulfonated carbohydrates has been predominantly that of sucralfate (AN 54182-58-0, sucrose octakis (hydrogen sulfate) aluminum complex). U.S. Pat. No. 3,432,489 describes the synthesis of various carbohydrate polysulfates and their aluminum complexes, including sucralfate. Norikawa, H., et al, in J. Chem. Soc. Faraday Trans. 1, 77(3), 629–39 (1981) described a structural analysis on the amorphous sodium salt and the amorphous aluminum hydroxide salt of sucrose sulfate using x-ray scattering intensity data. Making assumptions based on the single crystal structure previously determined for the potassium salt of sucrose octasulfate, the authors propose a structure for the sodium salt. Referring to the proposed structure of the sodium salt, a structure for the aluminum hydroxide salt is proposed. A description of the physiochemical properties of sucralfate is given by Nagashima, R. et al. in Arzneim. Forsch., 29 (11), 1668 (1979). The clinical use of sucralfate has been described by Nagashima R., et al., J. Clin. Gastroenteral., 3, 103 (1981) and its mode of action is described by Koba, H., SAMJ, 74 (Suppl 2 July), 43–44 (1988). The references cited above do not refer to a sucralfate-like compound which is characterized as having the unique physicochemical characteristics and unexpectedly useful physical and biological properties described hereafter.

The bibliography of sucralfate publications is extensive due to the product being on the market around the world for many years. The publications outlined herein and in the predecessor applications are believed to be most pertinent to the present invention and to be representative of the state of the prior art.

SUMMARY OF THE INVENTION

The object of this invention is to describe and claim (1) a chemical method which will produce a useful new sucralfate-like chemical compound as well as (2) the compound itself. Also certain new pharmaceutical applications and advantages of the product of this invention are described. The method comprises adding at least an eightfold stoichiometric quantity of aluminum chlorohydrate (8 molar equivalents) to sucrose octaammonium sulfate in an alcoholic medium. A granular, free-flowing sucralfate-like powder separates which, in turn, forms a viscid, biologically active compound upon contact with an aqueous liquid regardless of the pH of that liquid.

DETAILED DESCRIPTION OF THE INVENTION

Figure 1A:
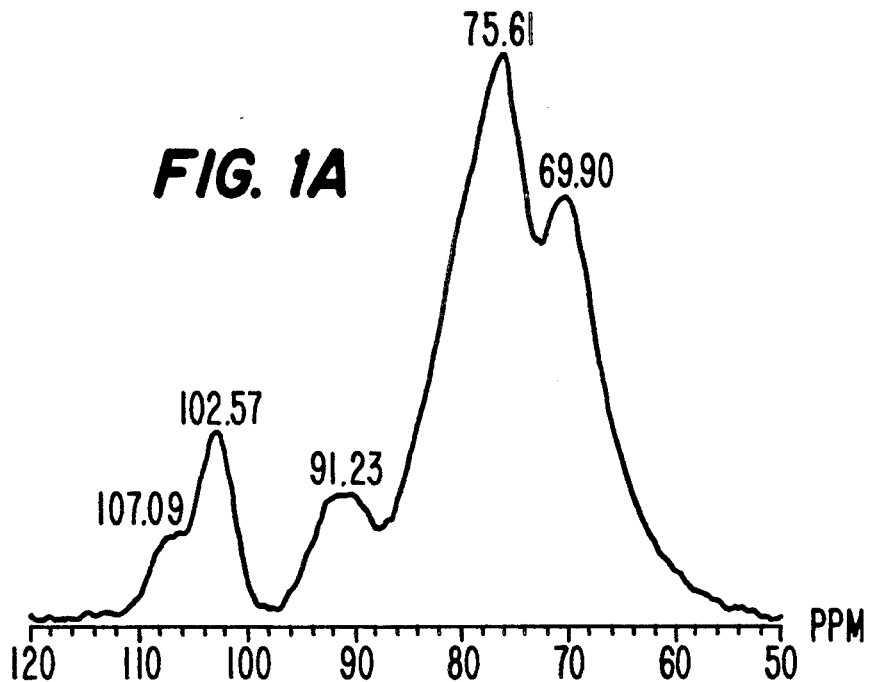
FIG. 1 describes the results of a $^{13}$C-nuclear magnetic resonance spectral analysis of sucralfate (FIG. 1A) and AAI-10001 (FIG. 1B).

The initial chemical step of the over all chemical process is the reaction of a purified powdered sucrose quantity with a previously prepared solution of an eightfold quantity of chlorosulfonic acid and either pyridine, or preferably, 2-picoline. The use of these reagents, especially 2-picoline, enables one to use a wider range of reaction temperatures in the first step of process. The time of reaction is up to 1-2 hours or until the reaction is substantially complete. The use of 2-picoline as solvent reactant has been found to give good yields and purity of product compared with the use of pyridine.

The reaction mixture of the sucrose octasulfate is then reacted with an excess of aqueous ammonia, usually in situ, to produce the ammonium salt which is easily isolated by treatment of the mixture with an alcohol such as methanol, ethanol or 2-propanol. The intermediate salt product is obtained in quantitative yield of 80-90% pure salt. One recrystallization from aqueous ethanol gives a product purity of 95-100%. This part of the chemical process has been claimed in the predecessor applications.

During the chemical process development for preparing high purity sucralfate, it was found that the reactants often formed a sticky end product material which adhered to glassware and other equipment. The product was useless because of its physical characteristics. Changing the order of reactants and using alcoholic media yielded high purity sucralfate. This is the subject of the immediate predecessor application.

Unexpectedly, in alcoholic media when the order of reaction is reversed from that described and claimed in the predecessor patent application (which was used to prepare high purity sucralfate using alcoholic solvents), a granular, free-flowing solid separates from the reaction mixture. This solid is white, free-stirring, irregularly shaped and easily isolatable by filtration. To date in our laboratory it forms only under the conditions described herein. More specifically, a solution of at least 8 equivalents of aluminum chlorohydrate (Al$_2$(OH)$_5$Cl·2H$_2$O) in ethanol or methanol is added slowly at ambient temperature to a solution of sucrose octaammonium sulfate in aqueous ethanol or methanol. The white powder which precipitates during the reaction is easily separated and purified by washing with various solvents especially ethanol, methanol or acetone. Depending on the solvent used in the final wash, the solid product may turn into a glassy solid upon drying. This solid can be ground to a fine consistency and used as such. Other solvents used in the synthesis, such as water, or aqueous mixtures of acetonitrile, acetone, isopropanol, n-propanol, N, N-dimethyl formamide, and ethylene glycol do not yield the desired product. While the overall chemical process varies slightly from that which yields sucralfate, the product of this synthesis (hereinafter designated AAI-10001) has physicochemical characteristics unique to this invention.

The solid product of this invention forms a viscid material in contact with any aqueous media not containing a significant quantity of organic modifiers under alkaline, acidic, neutral or isotonic conditions. Sucralfate, in a significant difference, forms an active, viscid material only when in contact with aqueous acids as in the gut.

The compound of this invention is insoluble in methanol, ethanol, isopropanol, propanol, acetone, N,N-dimethylformamide, acetonitrile, chloroform, methylene chloride, carbon tetrachloride and tetrahydrofuran. It forms a biologically active, viscid substance with water. It is soluble with degradation in mineral acids.

This invention has been distinguished from sucralfate by repeated analysis, by infrared spectroscopy, nuclear magnetic resonance spectroscopy, Raman spectroscopy and elemental analysis.

Figure 1B:
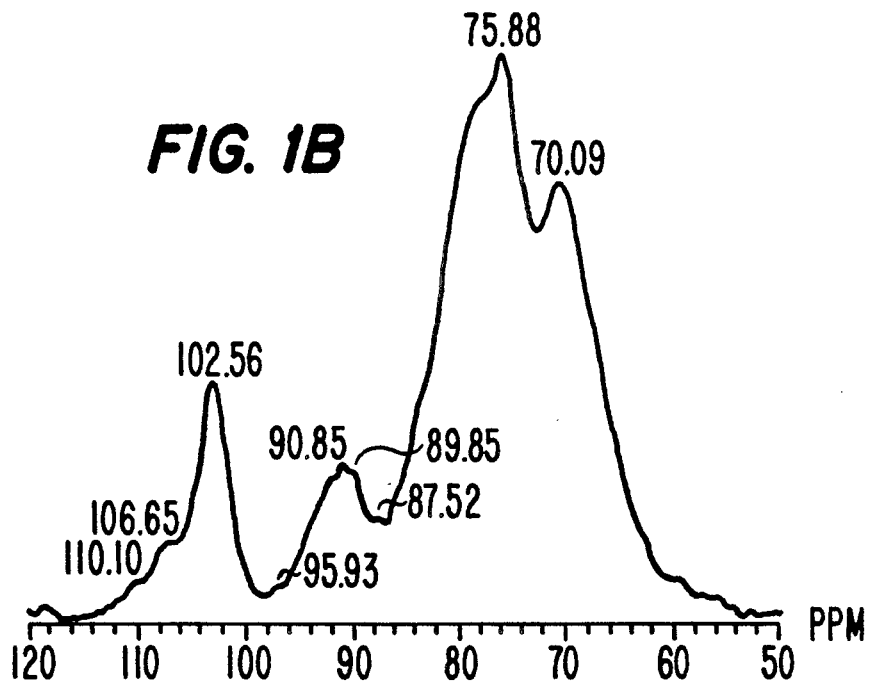

The 68 MHz solid state $^{13}$C-nuclear magnetic resonance spectra of multiple preparations of sucralfate and the compound of this invention were compared. The influence of the aluminum ions on the carbon nuclei broaden the spectral peaks; however, a major difference is repeatedly observed. There is a shoulder in the claimed compound at about 78.5 ppm which is absent in sucralfate. The remaining portions of the spectra are similar. FIG. 1 represents typical spectra.

Figure 2A:
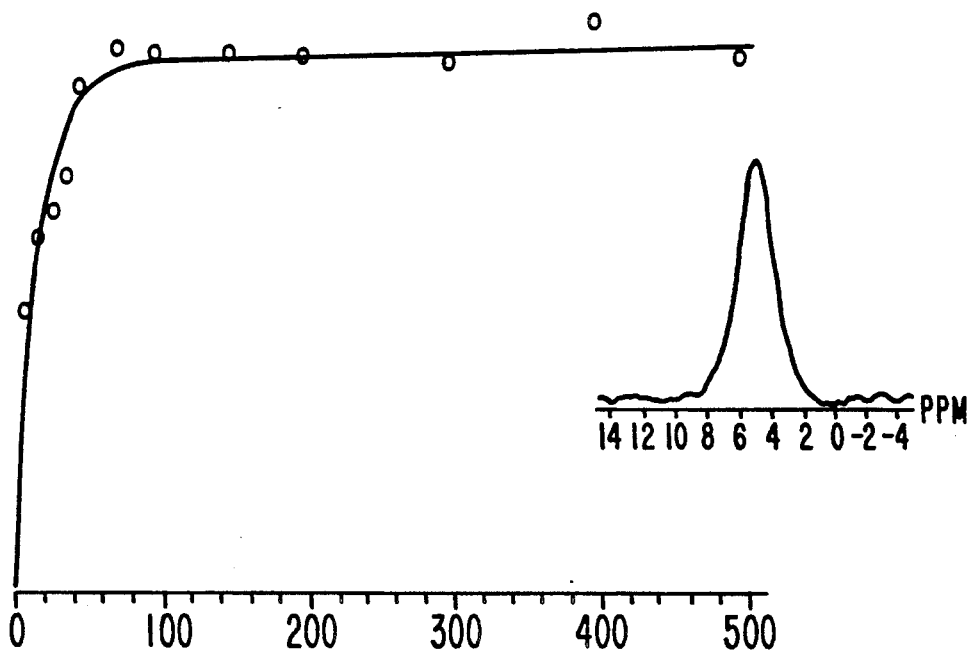
FIG. 2 describes the results of a 1-H nuclear magnetic resonance spectral analysis of sucralfate (FIG. 2A) and AAI-10001 (FIG. 2B).
Figure 2B:
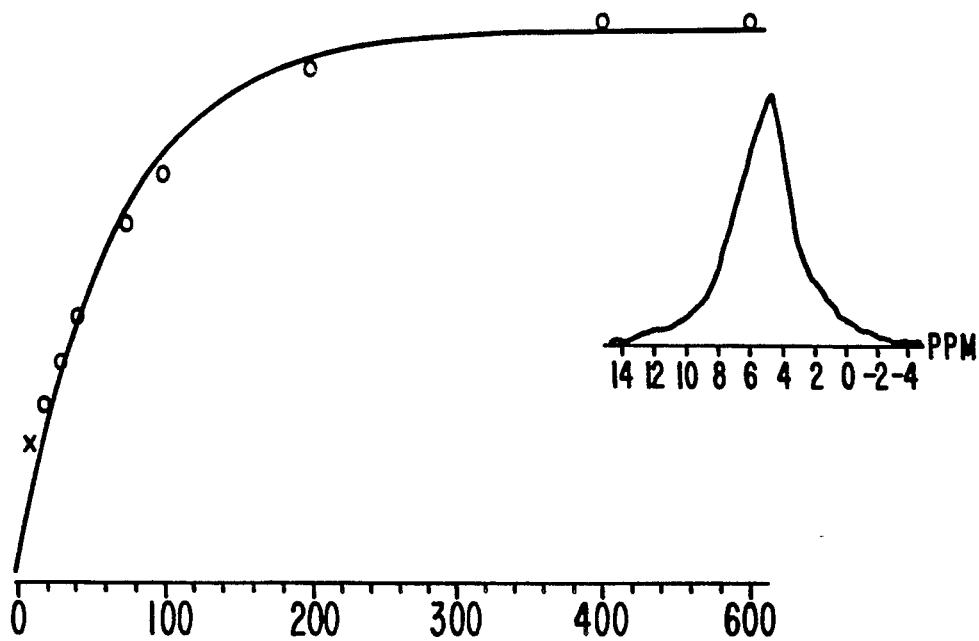

Solid state $^1$H-nuclear magnetic resonance studies comparing the compound of this invention (FIG. 2B) and sucralfate (FIG. 2A) were conducted. Such spectra typically exhibit broad lines. For this class of molecule the lines are especially broad due to the influence of aluminum. The spectra of this class of molecule (aluminum hydroxide complexes of organics) are dominated by the $^1$H of the —OH group. The spectra of both sucralfate and the compound of the invention are similar in that they exhibit a single broad peak with no fine structure. Closer inspection of the broad peaks indicates that the peak widths of the two materials are different. Peak width is a measure of the spin-lattice relaxation time, $T_1$, of the population of protons giving that peak. Using the progressive saturation technique, $T_1$'s were measured for four samples of sucralfate and four preparations of the compound of this invention. The results of the study are given in Table 1. These data suggest that the chemical environment of the hydroxyl protons are different in AAI-10001 than in sucralfate. FIG. 2 represents typical determinations using this technique.

TABLE 1

| Results of $T_1$ Measurements on Sucralfate and AAI-10001 | | | |
| --- | --- | --- | --- |
| Sample Sucralfate | $T_1$(msec) | Sample | $T_1$(msec) |
| A | 19.3 + 1.8 | AAI-10001-A | 67.0 + 3.1 |
| B | 15.2 + 1.1 | AAI-10001-B | 44.9 + 3.7 |
| C | 13.5 + 1.5 | AAI-10001-C | 66.3 + 3.5 |
| D | 12.2 + 2.4 | AAI-10001-D | 35.0 |
|   | x = 15.1 msec |   | x = 53.3 msec |

Figure 3A:
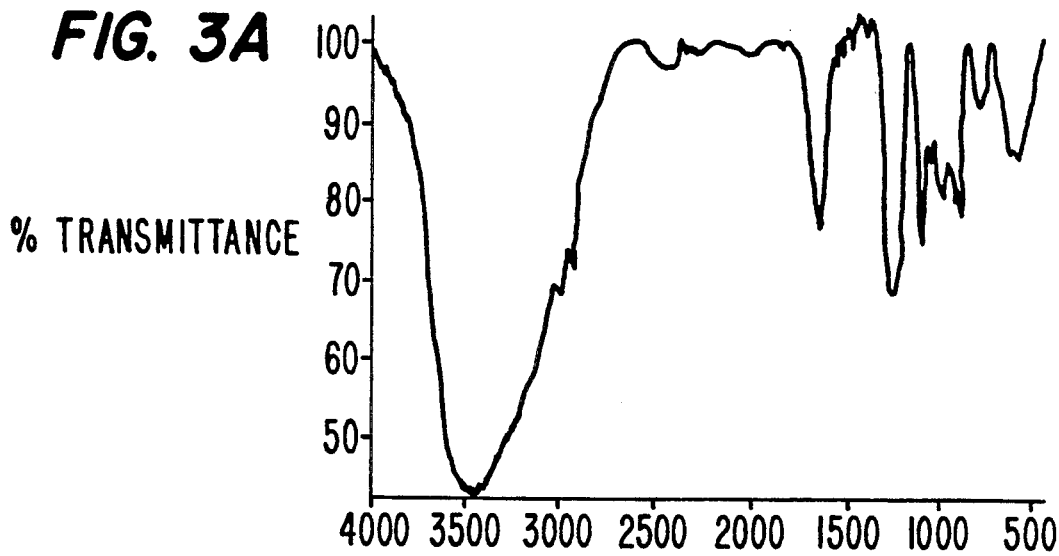
FIG. 3 describes the results of an infrared spectral analysis of sucralfate (FIG. 3A and FIG. 3B) and AAI-10001 (FIG. 3C).
Figure 3B:
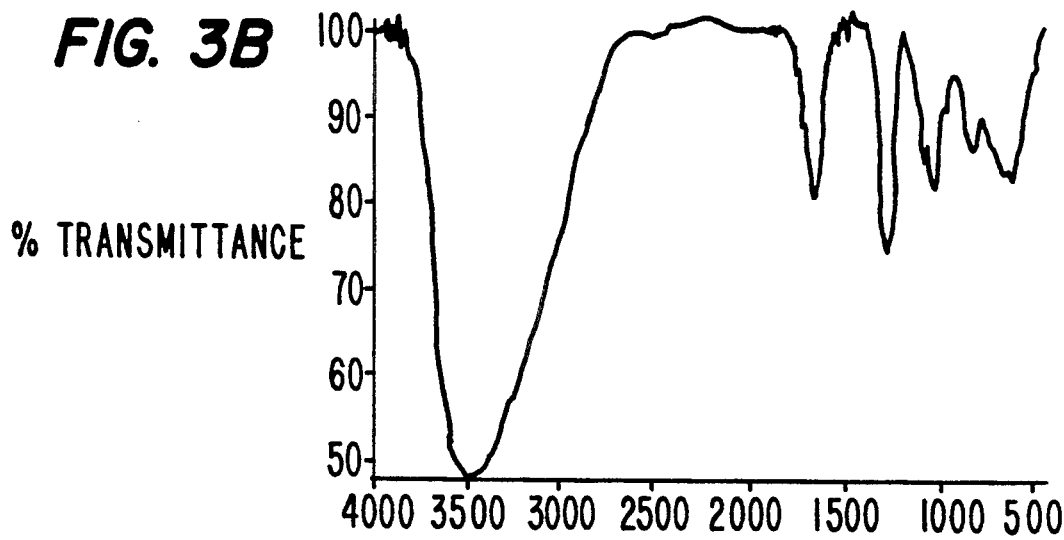
Figure 3C:
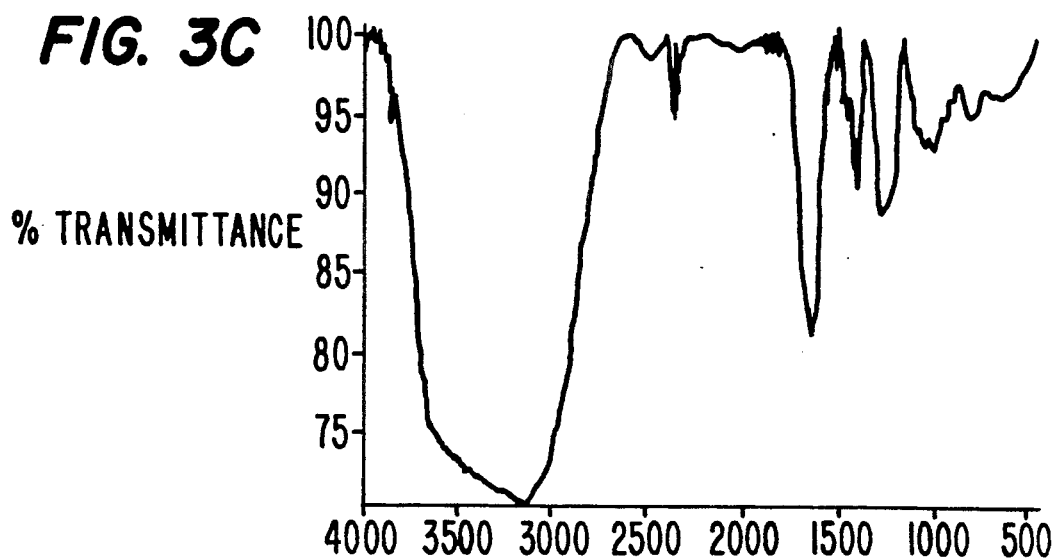
Figure 4A:
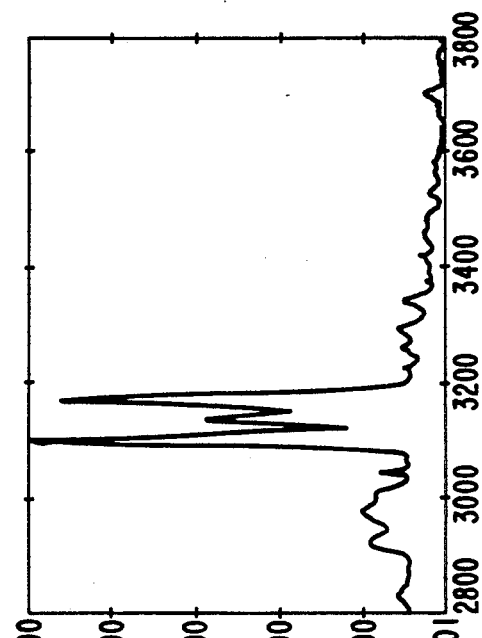
FIG. 4 describes the results of a Raman spectral analysis of sucralfate (FIG. 4A and FIG. 4C) and AAI-10001 (FIG. 4B and FIG. 4D).
Figure 4C:
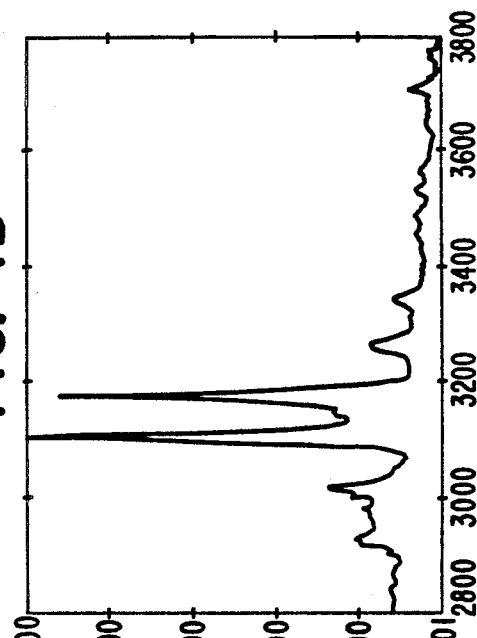
Figure 4B:
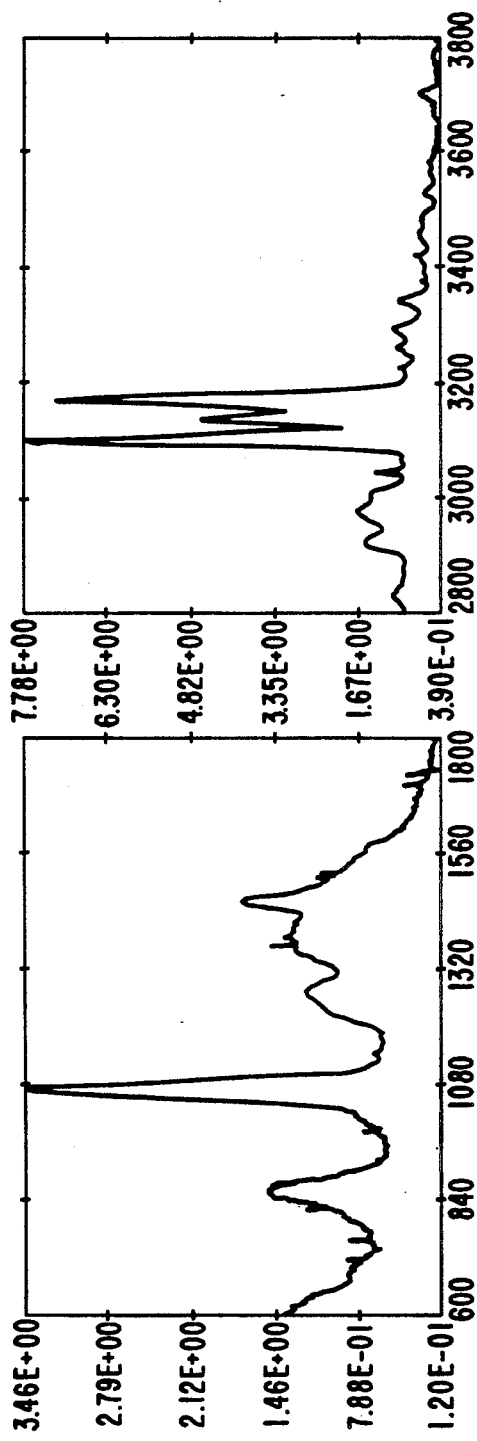
Figure 4D:
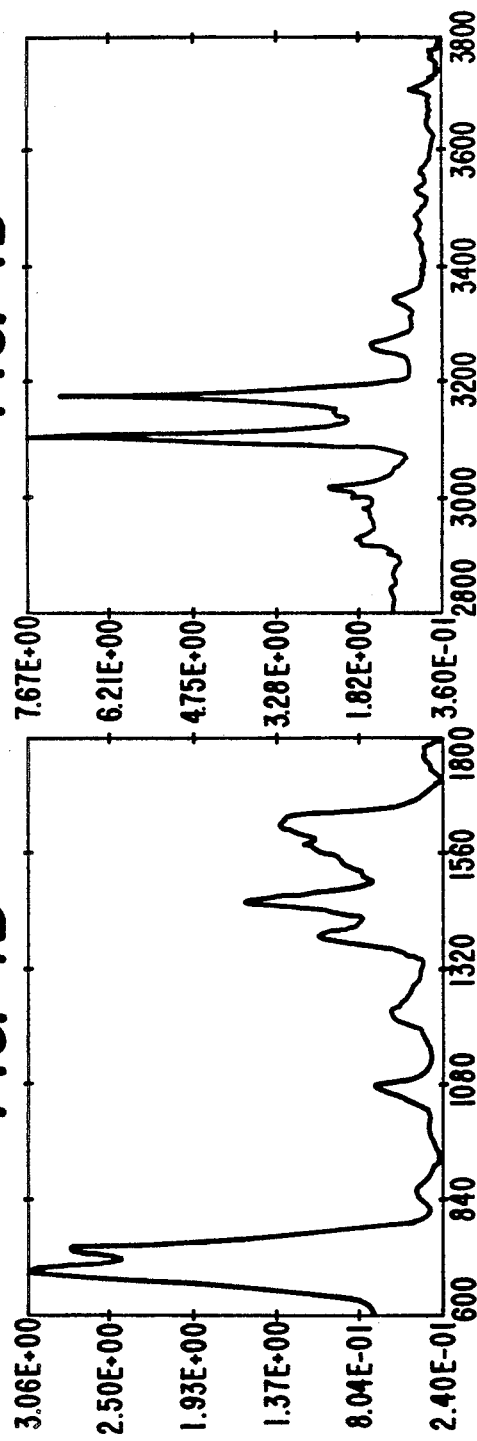

A comparison of the potassium bromide dispersion infrared spectra of AAI-10001 (FIG. 3C) and sucralfate (FIG. 3A and FIG. 3B) further demonstrate the structural differences of these materials. The spectra show the presence of $H_2O$, and the —OH and —$OSO_3$ functional groups in both materials. However, the claimed compound has an additional strong band at approximately 1385 to 1405 cm$^{-1}$ and a weaker band at approximately 1450 to 1460 cm$^{-1}$. Additionally, AAI-10001 has a much broader band in the 2800–3600 cm$^{-1}$ band due to the additional strong band in the 2800 to 3000 cm$^{-1}$ region. Together, these three bands indicate the presence of the ammonium ion ($NH_4^+$). The infrared spectrum of sucralfate is lacking these bands. These differences in infrared spectra were found repeatedly. FIG. 3 exhibit typical infrared spectra.

The Raman spectra of sucralfate (FIG. 4A and FIG. 4C) and AAI-10001 (FIG. 4B and FIG. 4D) were compared. There are significant differences in band intensity and location. FIG. 4 depicts these differences. Significant differences are seen in the 600 cm$^{-1}$ to 1806 cm$^{-1}$ fingerprint region of the spectrum indicating different chemical structure. In the hydroxyl region (2000 cm$^{-1}$ to 3800 cm$^{-1}$) there are more subtle differences in band ratios and locations. These differences further indicate that the two molecules are distinct.

The spectral properties of the compound of this invention are repeatable and distinctive. While the exact molecular structure of the compound of this invention is not known and cannot be ascertained at this time, it appears that AAI-10001 may be the ammonium tetradeca-aluminum complex of sucrose octasulfate.

From the studies described herein, one skilled in the art will recognize that the new compound of this invention is unique. The free flowing white powder of this invention upon contact with any aqueous based liquid, for example, an acid, base, neutral or isotonic solution becomes a viscid semisolid which readily adheres to surfaces. It is well documented in the literature that sucralfate requires an acidic medium to form this viscid substance which is the putative ulcer treatment form of the drug, (R. Nagashima, J. Clin. Gastroenterol. 3,103–110 (1981)). The two molecules are clearly different in this physical property.

Since the product of this invention becomes viscid in aqueous neutral, basic or isotonic liquid media, it has a potential advantage for the medical profession. It could enable sucralfate-like treatment of the neutral gut by co-administration with acid reducing agents, such as $H_2$-antagonists, atropine-like agents or inorganic neutralizing agents such as calcium carbonate or bicarbonate. Further, the product of this invention can be employed to treat abnormal surface conditions such as wounds, ulcers, open cysts, abrasions and the like by direct application to the wound site where isotonic body fluids turn the granular compound into the active viscid substance at the wound site.

The product of this invention is able to be incorporated into various pharmaceutical dosage unit forms for internal (oral) administration or for topical administration to the skin, oral cavity or rectal cavity. Such may be tablets, granules, suspensions, capsules, caplets, candies, troches, powders, as well as bandages, dressings, ointments or suppositories. The doses for oral administration are the same regimens as those used for sucralfate. The topical preparations will contain up to 5% active ingredient. For oral administration, the compound may be combined with another anti-ulcer agent as well. The pharmaceutical carriers may be any orally acceptable liquid or solid dosage unit form.

As mentioned above, the last step chemical reaction of this invention is essentially dependent on the solvent system used and on the order of addition of the reactants. About 8 mole-equivalents of aluminum chlorohydrate ($Al_2(OH)_5Cl \cdot 2H_2O$) in an alcoholic solvent is added slowly to one equivalent of sucrose octaammonium sulfate in the same solvent. An excess of the aluminum salt may be used to insure complete complex formation. Ambient temperature is preferred. Variations of temperature have not been found to be critical.

The organic cosolvent for the aqueous reaction is critical, with methanol and ethanol yielding product having good handling properties. Aqueous mixtures may run from about 20% to 80% alcohol in water. Preferably from about 20% to 40% is used depending on the alcohol. Ethanol is the preferred cosolvent. The most pertinent prior art, U.S. Pat. No. 3,432,489, mentioned hereinabove discloses only water as the solvent in the preparation of sucralfate. The critical nature of the solvent is demonstrated by the fact that running the reaction in water alone or other water miscible organic solvents as a solvent does not give the desired and indicated physicochemical characteristics of the product of this invention.

The course of the reaction proceeds promptly, usually within 1-3 hours of addition time, with the claimed complex separating from solution. The product is separated, washed and dried to give the desired product.

The following examples are embodiments of this invention and should not be construed as limiting its scope.

Example 1

Chlorosulfonic acid (394.4 g, 3.39 mole) is slowly added to 2-picoline (1226 g, 13.2 mole) while the temperature is maintained at 40°-50° C. with vigorous stirring. Finely powdered sucrose (140 g, 0.41 mole) is added and the mixture is stirred for an additional one hour at 55°-65° C. Aqueous ammonia (14%) is added to bring pH to 7.5-8.0 while temperature is maintained below 30° C. Reagent alcohol (0.5 L) is added and stirring is continued until an oily product is solidified. The solid product is filtered, washed with reagent ethanol (400 ml) and dried under vacuum (0.5 mm Hg) at 45°-50° C. for twelve hours. This product is recrystalized from 1000 ml aqueous reagent ethanol (50/50) to produce 441 g (69%) of pure sucrose octasulfate ammonium salt.

Sucrose octasulfate sodium salt is optionally prepared by dissolving sucrose octasulfate ammonium salt (20 g) in water (100 ml). Aqueous sodium hydroxide (20%) is added to bring the pH to 8-9. Reagent ethanol is added to precipitate sucrose octasulfate sodium salt. This salt is filtered and dried as in the case of the ammonium salt.

38 ml of a 50% aqueous ethanolic solution of aluminum chlorohydrate, ($Al_2(OH)_5Cl \cdot 2H_2O$) (0.120 moles), is diluted with 38 ml of a 60% aqueous ethanol solution. This solution is added dropwise with stirring at ambient temperature over 1-3 hours into a solution of sucrose octaammonium sulfate (0.015 moles in 750 ml of 60% aqueous ethanol).

The white powder precipitate is separated by centrifuging and washed with copious amounts of 60% aqueous ethanol.

The wet material can be used as such or dried at 50° C. for 4 hours. The yield is approximately 100%.

The as-is purity of this material is 81.6% and the anhydrous purity is 97.6%. This material is the free flowing powder mentioned above and is particularly useful for both the internal and, particularly, external treatment of wounds.

Analytical values of four typical runs of the process are as follows (corrected for water).

| | % | | | | | |
|---|---|---|---|---|---|---|
| | C | H | N | S | Al | O |
| AAI-10001-E | 6.89 | 3.07 | 0.9 | 12.36 | 19.0 | — |
| AAI-10001-A | 7.03 | 2.67 | 1.0 | 12.08 | 19.5 | — |
| AAI-10001-B | 7.25 | 3.10 | 1.16 | 11.53 | 19.2 | — |
| AAI-10001-C | 7.25 | 3.00 | 1.10 | 12.09 | 18.8 | — |
| x | 7.11 | 2.96 | 1.04 | 12.03 | 19.1 | — |
| Standard deviation (+, −) | 0.18 | 0.20 | 0.11 | 0.33 | 0.30 | — |
| Sucralfate (Theoretical) | 6.91 | 2.61 | 0 | 12.29 | 20.69 | 57.50 |

EXAMPLE 2

Sucrose octasulfate, ammonium salt is prepared as described in Example 1.

19 ml of a 50% solution of aluminum chlorohydrate is diluted with 19 ml of a 60% aqueous methanol. This solution is added dropwise with stirring at ambient temperature over ½ hour into a solution of sucrose octasulfate ammonium salt (9.08 g in 375 ml of 60% aqueous methanol). The white powder is filtered and dried under vacuum. Total weight is 16.43 g. The as-is purity of this material is 76.8 and the anhydrous purity is 90.5%.

| | % | | | |
|---|---|---|---|---|
| | C | H | N | S |
| AAI-10001-F | 6.75 | 2.56 | 1.08 | 12.23 |

What is claimed is:

1. A chemical process for preparing an aluminum complex of polysulfonated sucrose comprising reacting at least 8 molar equivalents of aluminum chlorohydrate with 1 molar equivalent of sucrose octaammonium sulfate in a medium selected from the group consisting of an ethanolic medium and a methanolic medium by adding said aluminum chlorohydrate in said medium slowly to said sucrose octaammonium sulfate in said medium.

2. The process of claim 1 in which aqueous ethanol is the medium.

3. The process of claim 2 in which the aqueous ethanol is 20-40% ethanol.

4. The process of claim 2 in which the reaction time is from 1 to 3 hours.

5. The process of claim 2 in which the precipitated product is removed, washed with an alcoholic solvent or acetone, dried and ground.

6. A chemical compound which is prepared by the process of claim 1 and which:
   (A) is a white, free-flowing powder comprising irregularly sized particles;
   (B) has a general structural similarity to sucralfate; and
   (C) has structural differences from sucralfate which are demonstrated by:
      (a) having a shoulder peak at about 78.5 p.p.m. in the solid state $^{13}C$-nuclear magnetic resonance spectrum;

(b) having a $T_1$ relaxation time about three times higher than that of sucralfate by solid state $^1$H-nuclear magnetic resonance spectroscopy;
(c) having a clear, broad band at 1385 cm$^{-1}$ to 1405 cm$^{-1}$ and a broader band in the 2800 to 3600 cm$^{-1}$ region when compared with sucralfate by the infrared spectroscopy;
(d) having a Raman spectrum differing from that of sucralfate in the 2000 cm$^{-1}$ to 3800 cm$^{-1}$ and 600 cm$^{-1}$ to 1806 cm$^{-1}$ regions with a strong band at 600 to 840 cm$^{-1}$ and a depressed band at 1080 cm$^{-1}$ present in the Raman spectrum of said chemical compound;
(e) being converted to a biologically active, viscid physical form upon contact with a neutral, basic, acid or isotonic aqueous medium; and
(f) being generally insoluble in organic solvents.

7. A pharmaceutical composition having wound healing activity which comprises a non-toxic, effective therefor quantity of the compound of claim 6 in association with a pharmaceutical carrier.

* * * * *